United States Patent
Fowler et al.

(10) Patent No.: US 9,446,006 B2
(45) Date of Patent: Sep. 20, 2016

(54) HYDROXYTYROSOL COMBINATIONS FOR ENHANCING MITOCHONDRIAL FUNCTION AND ENERGY PRODUCTION

(71) Applicants: Ann Fowler, Rheinfelden (CH); Angelika Friedel, Binzen (DE); Darko Knutti, Riehen (CH); Karin Kuratli, Reinach (CH); Daniel Raederstorff, Flaxlanden (FR); Ying Wang-Schmidt, Stallikon (CH); Karin Wertz, Rheinfelden (DE)

(72) Inventors: Ann Fowler, Rheinfelden (CH); Angelika Friedel, Binzen (DE); Darko Knutti, Riehen (CH); Karin Kuratli, Reinach (CH); Daniel Raederstorff, Flaxlanden (FR); Ying Wang-Schmidt, Stallikon (CH); Karin Wertz, Rheinfelden (DE)

(73) Assignee: DSM IP ASSETS B.V., Heerlen (NL)

( * ) Notice: Subject to any disclaimer, the term of this patent is extended or adjusted under 35 U.S.C. 154(b) by 55 days.

(21) Appl. No.: 14/450,073

(22) Filed: Aug. 1, 2014

(65) Prior Publication Data

US 2015/0030579 A1    Jan. 29, 2015

Related U.S. Application Data

(62) Division of application No. 13/264,819, filed as application No. PCT/EP2009/063492 on Oct. 15, 2009, now abandoned.

(60) Provisional application No. 61/202,888, filed on Apr. 17, 2009.

(30) Foreign Application Priority Data

Apr. 17, 2009   (WO) ................. PCT/EP2009/054585

(51) Int. Cl.
| | |
|---|---|
| *A61K 31/05* | (2006.01) |
| *A61K 31/122* | (2006.01) |
| *A61K 31/522* | (2006.01) |
| *A61K 31/195* | (2006.01) |
| *A61K 31/51* | (2006.01) |
| *A61K 31/19* | (2006.01) |
| *A61K 31/145* | (2006.01) |
| *A61K 31/34* | (2006.01) |
| *A61K 31/352* | (2006.01) |
| *A61K 31/4188* | (2006.01) |
| *A61K 31/525* | (2006.01) |
| *A61K 31/4406* | (2006.01) |
| *A23L 1/29* | (2006.01) |
| *A23L 1/30* | (2006.01) |
| *A23L 1/302* | (2006.01) |
| *A23L 1/305* | (2006.01) |
| *A23L 2/52* | (2006.01) |
| *A61K 31/197* | (2006.01) |
| *A61K 31/205* | (2006.01) |
| *A61K 31/4415* | (2006.01) |
| *A61K 31/455* | (2006.01) |
| *A61K 31/714* | (2006.01) |

(Continued)

(52) U.S. Cl.
CPC .............. *A61K 31/05* (2013.01); *A23K 20/111* (2016.05); *A23K 20/121* (2016.05); *A23K 20/147* (2016.05); *A23K 20/174* (2016.05); *A23L 1/296* (2013.01); *A23L 1/30* (2013.01); *A23L 1/3002* (2013.01); *A23L 1/302* (2013.01); *A23L 1/3004* (2013.01); *A23L 1/3051* (2013.01); *A23L 2/52* (2013.01); *A61K 31/122* (2013.01); *A61K 31/145* (2013.01); *A61K 31/19* (2013.01); *A61K 31/195* (2013.01); *A61K 31/197* (2013.01); *A61K 31/205* (2013.01); *A61K 31/34* (2013.01); *A61K 31/352* (2013.01); *A61K 31/4188* (2013.01); *A61K 31/4406* (2013.01); *A61K 31/4415* (2013.01); *A61K 31/455* (2013.01); *A61K 31/51* (2013.01); *A61K 31/522* (2013.01); *A61K 31/525* (2013.01); *A61K 31/714* (2013.01); *A61K 36/63* (2013.01); *A61K 45/06* (2013.01); *A23V 2002/00* (2013.01)

(58) Field of Classification Search
CPC .... A61K 31/05; A61K 31/122; A61K 36/63; A61K 31/522; A61K 31/195; A61K 31/19; A61K 31/51; A61K 31/145; A61K 31/34; A61K 31/352; A61K 31/4188; A61K 31/525; A61K 31/4406; A61K 31/714; A23L 1/3004
USPC ........... 424/94.1; 514/263.34, 393, 456, 473, 514/52, 561, 565, 665, 733
See application file for complete search history.

(56) References Cited

U.S. PATENT DOCUMENTS 8,841,264 B2 * 9/2014 Raederstorff .......... A61K 31/05
514/32

FOREIGN PATENT DOCUMENTS

| EP | 1 714 658 | 10/2006 |
| EP | 1 982 706 | 10/2008 |
| JP | 2006-506361 | 2/2006 |

(Continued)

OTHER PUBLICATIONS

Romero et al. Analysis of Total Contents of Hydroxytyrosol and Tyrosol in Olive Oils. J. Agric. Food Chem. 60:9017-9022, 2012.*

(Continued)

*Primary Examiner* — Clinton Brooks
*Assistant Examiner* — Yih-Horng Shiao
(74) *Attorney, Agent, or Firm* — Nixon & Vanderhye P.C.

(57) ABSTRACT

Hydroxytyrosol or olive juice containing hydroxytyrosol in combination with at least one of the compounds selected from the group consisting of: creatine, coenzyme Q10, resveratrol, caffeine, carnitine, B vitamins (B1, B2, B3, B5, B6, and/or B12) and ginseng (preferably: root) extract.can be used to maintain or increase mitochondrial biogenesis in cardiac muscle, skeletal muscles, and liver tissue.

6 Claims, 15 Drawing Sheets

(51) Int. Cl.
*A61K 36/63* (2006.01)
*A61K 45/06* (2006.01)

(56) References Cited

FOREIGN PATENT DOCUMENTS

| | | |
|---|---|---|
| JP | 2009-511522 | 3/2009 |
| WO | 2004/032873 | 4/2004 |
| WO | 2007/042271 | 4/2007 |
| WO | WO2007/112996 | * 10/2007 |
| WO | 2008/006581 | 1/2008 |
| WO | 2008/128552 | 10/2008 |
| WO | 2008/128629 | 10/2008 |
| WO | 2009/144093 | 12/2009 |

OTHER PUBLICATIONS

International Search Report for PCT/EP2009/063492, mailed Feb. 5, 2010.

Vékey et al, *Biophenol—Protein Supramolecular Models by Fast Atom Bombardment—Mass Spectrometric Experiments,* J. Agric. Food Chem. 1997, 45, 2447-2451.
Ali Ibn-e-Abbaas Majoosi Kaamil-al-Sena'ah, Part II (10th century AD) Page(s) being submitted—05 (p. No. 04-08) (Ref.pg. No. of publication:105) Publication Date—2005 AD Publisher—Central Council for Research in Unani Medicine Place of Publication—New Delhi, India.†
Abu Bakr Mohammad Bin Zakariyya Al-Razi Kitaab-al-Haawi-fil-Tibb, vol. XX (9th century AD) Page(s) being submitted—04 (p. No. 09-12) (Ref.pg. No. of publication:555) Publication Date—1967 AD Publisher—Dayerah-al-Ma'aarif Usmania, Place of Publication—Hyderabad, India.†
Aminuddaulah Abul Farj Ibn Al-Quff Maseehi Kitaab-al-'Umdah-fil-Jeraahat, Part II (13th century AD) Page(s) being submitted—04 (p. No. 13-16) (Ref.pg. No. of publication:237) Publication Date—1937 AD Publisher—Dayerah-al-Ma'aarif Usmania Place of Publication—Hyderabad, India.†

\* cited by examiner
† cited by third party

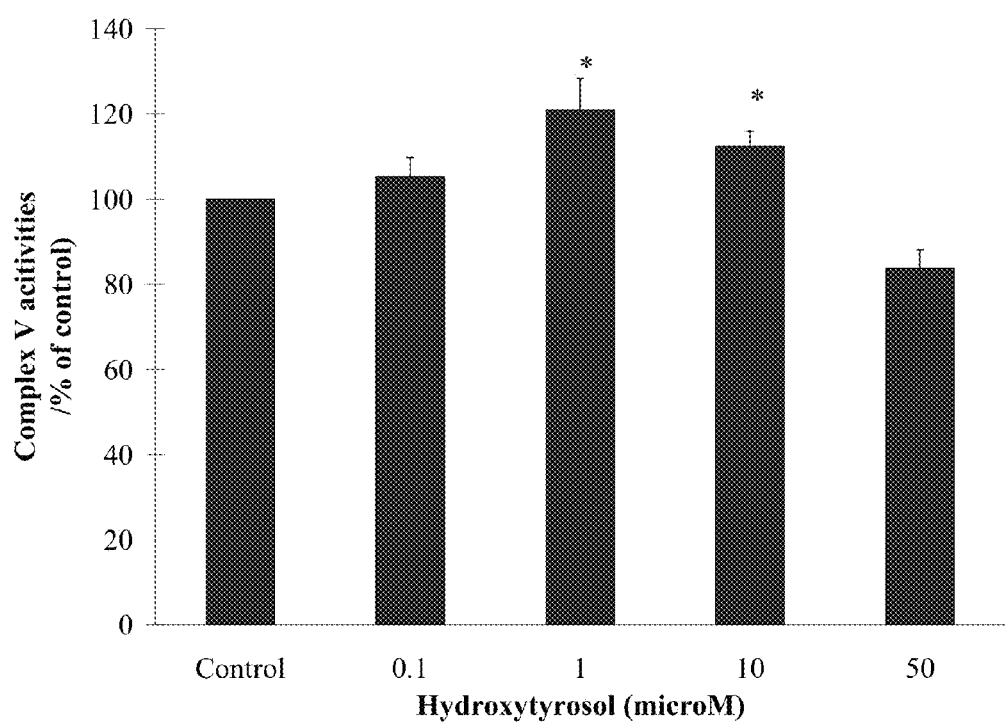

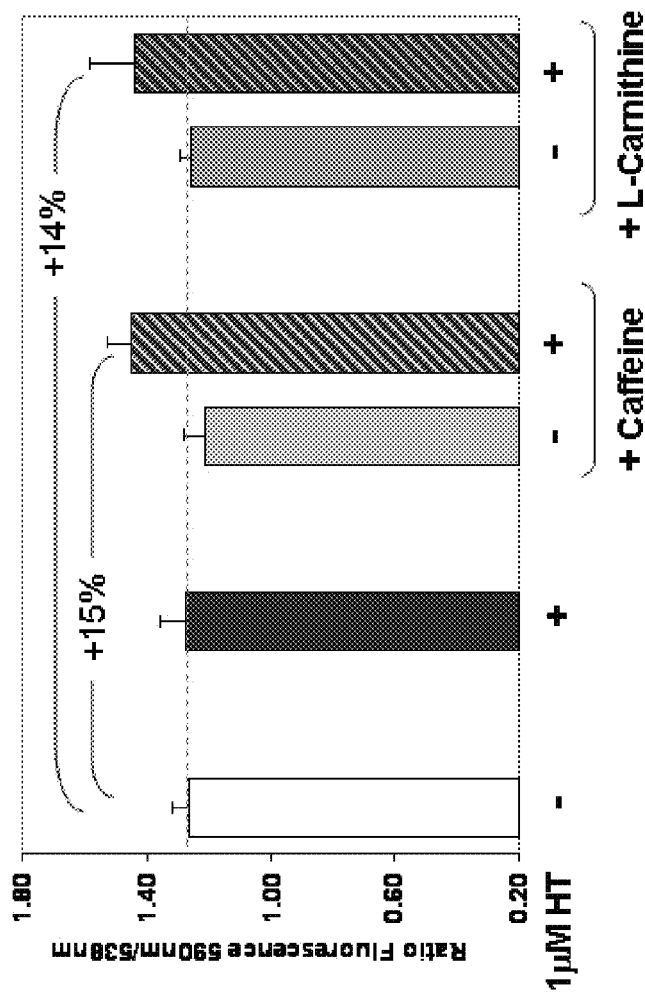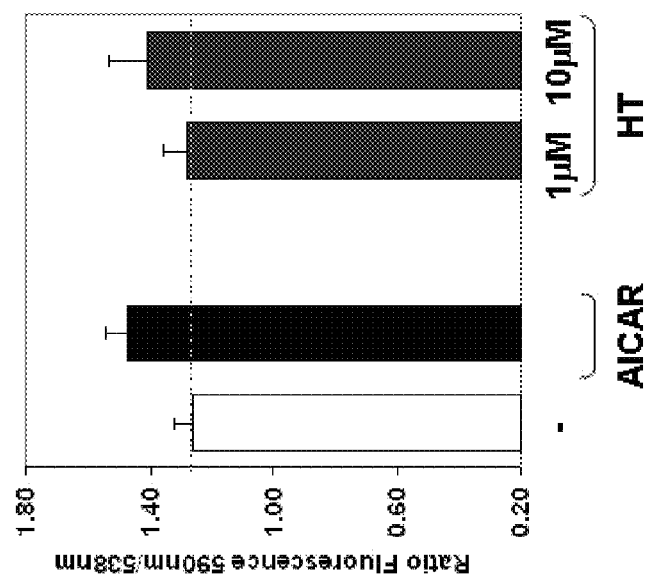

HYDROXYTYROSOL COMBINATIONS FOR ENHANCING MITOCHONDRIAL FUNCTION AND ENERGY PRODUCTION

CROSS-REFERENCE

This application is a divisional of commonly owned U.S. application Ser. No. 13/264,819, filed May 4, 2012 (now abandoned) which is the national phase application under 35 USC §371 of PCT/EP2009/063492, filed Oct. 15, 2009 which designated the U.S. and claims priority to EP Patent Application No. PCT/EP2009/054585, filed Apr. 17, 2009 and U.S. Provisional Application No. 61/202,888, filed Apr. 17, 2009, the entire contents of each of which are hereby incorporated by reference.

FIELD OF THE INVENTION

This invention is related to the use of hydroxytyrosol ("HT"), or a composition containing hydroxytyrosol or a precursor of hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, epigallocatechin (EGCG) and ginseng extract. These compositions synergistically enhance the body's own capacity for energy generation and/or enhance cellular energy generation. It also relates to pharmaceutical and nutraceutical compositions useful for conditions characterized by altered mitochondrial functioning and biogenesis, such as heart strength, various liver diseases, improve muscle/fat ratio and muscle endurance.

BACKGROUND OF THE INVENTION

Mitochondria are organelles in the cell responsible for aerobic energy production. The mitochondrial inner membrane is embedded with a respiratory chain containing complexes I, II, III, IV and V, which transport electrons and produce ATP via a series of redox reactions, a process called oxidative phosphorylation. The aerobic energy metabolism is more efficient than the anaerobic energy production. Anaerobic energy production involves the conversion of glucose to lactate (glycolysis), and generates only 8 Mol ATP per Mol glucose. During aerobic energy metabolism, glucose is completely oxidized (by glycolysis, Krebs cycle and the mitochondrial electron chain) to $CO_2$ and $H_2O$, while giving rise to 38 Mol ATP/mol glucose.

There is a critical metabolic fork in the road at the end of glycolysis. At this fork, glucose has been converted from one 6 carbon molecule to two, 3 carbon molecules called pyruvic acid, or pyruvate. This pyruvate can either be shuttled into the mitochondria via the enzyme pyruvate dehydrogenase, or converted to lactic acid via the enzyme lactate dehydrogenase. Entry into the mitochondria exposes the pyruvate to further enzymatic breakdown, oxidation, and a high ATP yield per glucose. This process inside the mitochondria ultimately requires oxygen molecules to proceed and is therefore "aerobic". Conversion to lactate means a temporary dead end in the energy yielding process, and the potential for contractile fatigue due to decreasing cellular pH if lactic acid accumulation proceeds unchecked.

In addition to their well known function of supplying energy to a cell, mitochondria and their components participate in a number of other cellular activities. For example, mitochondria also control thermogenesis and the apoptosis process and are thus involved in the ageing process.

The mitochondria contain a high level of oxidants, since the respiratory chain generates reactive species, e.g. superoxide anions, if it works with reduced efficiency or during energy uncoupling. Superoxide anions are generated as by-products in several steps of electron transport chain, such as the reduction of coenzyme Q in complex III, where a highly reactive free radical is formed as an intermediate (Q.-). This unstable intermediate can lead to electron "leakage", when electrons jump directly to oxygen and form the superoxide anion, instead of moving through the normal series of well-controlled reactions of the electron transport chain.

An antioxidant is a molecule capable of slowing or preventing the oxidation of other molecules. Antioxidants terminate oxidation chain reactions by removing free radical intermediates, and inhibit other oxidation reactions by being oxidized themselves. Reducing agents such as thiols or polyphenols often exert antioxidant property. Well known antioxidants such as Vitamin A, C and E scavenge free radicals and protect DNA, proteins and lipids from damage. Antioxidants also protect mitochondria from reactive oxygen species and free radicals generated during ATP production.

While it has been generally accepted in the past that administration of antioxidants would be beneficial to promote mitochondrial biogenesis, this has not been shown to be the case. Gomez-Carbera et al. 2008 *Am. J Clin. Nutr.* 87(1):142-149, demonstrated in a double-blinded randomized clinical study, that oral administration of 1 g Vitamin C per day actually resulted in decreased mitochondrial biogenesis in skeletal muscle.

Hydroxytyrosol has been described in the past as having positive cardiovascular effects (see, e.g. Gonzalez-Santiago et al 2006 *Atherosclerosis* 188:35-42; or Mitro et al 2003 *NMCD. Nutritional Metabolism and Cardiovascular Diseases* 13(5):306) but these are concerned with the anti-atherosclerotic effects of hydroxytyrosol and/or its status as an antioxidant.

BRIEF DESCRIPTION OF THE FIGURES

FIGS. 5A-5E show the effect of treatment with hydroxytyrosol on activities of complexes in adipocytes, wherein FIG. 5A shows the effect for Complex I, FIG. 5B shows the effect for Complex II, FIG. 5C shows the effect for Complex III, FIG. 5D shows the effect for Complex IV, and FIG. 5E shows the effect for Complex V, respectively. Adipocytes were treated with different concentrations of hydroxytyrosol for 48 hrs. Values are mean±SE of data from three separate experiments for complex I, and six separate experiments for complex II and III, and each experiment was performed in duplicate.*p<0.05, **p<0.01 vs. control.

FIGS. 8A and 8B show synergistic effects of hydroxytyrosol in combination with caffeine or L-carnitine on the mitochondrial membrane potential in C2C12 cells, wherein FIG. 8A is a graph of AICAR and 10 uM hydroxytyrosol increase mitochondrial membrane potential, and FIG. 8B is a graph of combinations of 1 uM hydroxytyrosol with caffeine or with L-carnitine showing an increase of membrane potential synergistically. Relative mitochondrial membrane potential was assessed by the changes in red to green fluorescence emitted by the JC-1 dye. Cells were treated for 24 h with solvent (-), 500 uM AICAR (AICAR), 1 uM hydroxytyrosol or 100 uM hydroxytyrosol (HT), 200 uM caffeine (Caffeine), and/or 200 uM L-carnitine (L-Carnithine) as indicated. Data shown is the average of quadruplicates±standard deviation.

DETAILED DESCRIPTION OF THE INVENTION

Figure 1:
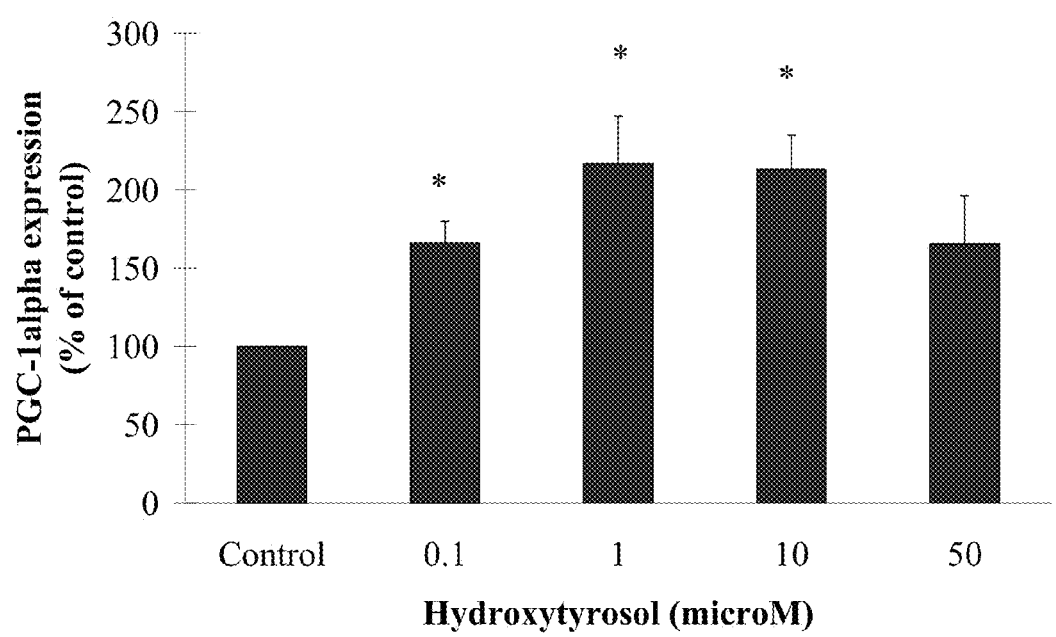
FIG. 1 shows expression of PGC-1α. Quantitative values tabulated for PGC-1α:α-tubulin ratio with a densitometry. Values are mean±SE of five experiments. * $p<0.05$ vs. control; **$P<0.01$ vs. control.
Figure 2A:
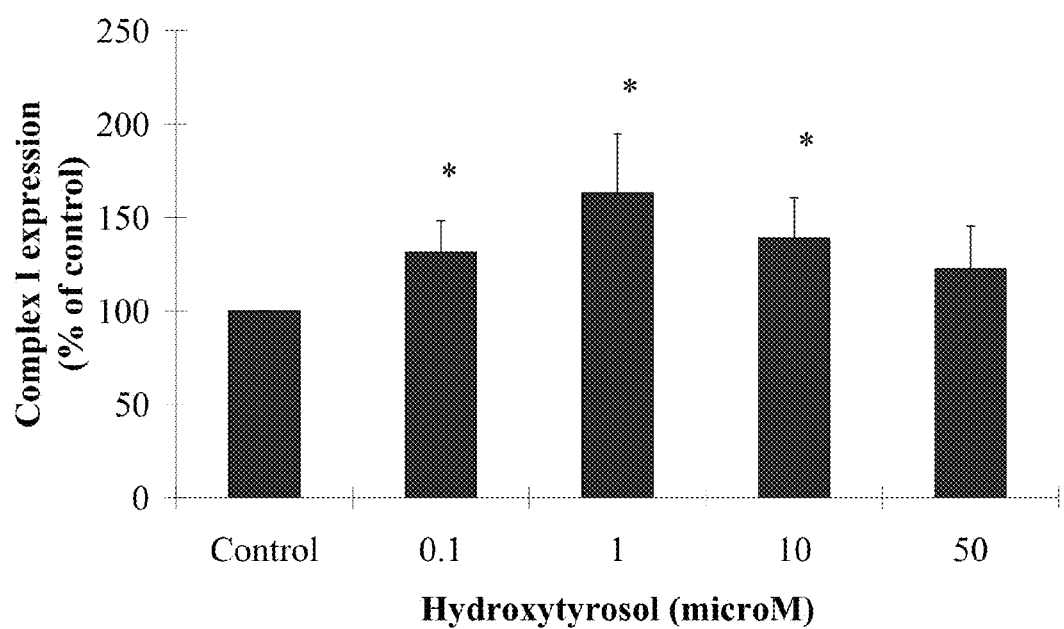
FIGS. 2A-2D show expressions of mitochondrial proteins. 3T3-L1 adipocytes were treated for 48 hrs with hydroxytyrosol. Cells were subsequently solubilized into SDS sample buffer and analyzed by Western blotting with antibodies against α-tubulin, mitochondrial electron transport complexes. The quantitative analyses of the bands by densitometry are shown in FIGS. 2A, 2B, 2C and 2D for mitochondrial complex I, complex II, complex III and complex IV, respectively. Results shown are fold increases from control from 4 independent experiments compared with control cells. *$p<0.05$ vs. control. **$p<0.01$ vs. control.
Figure 2B:
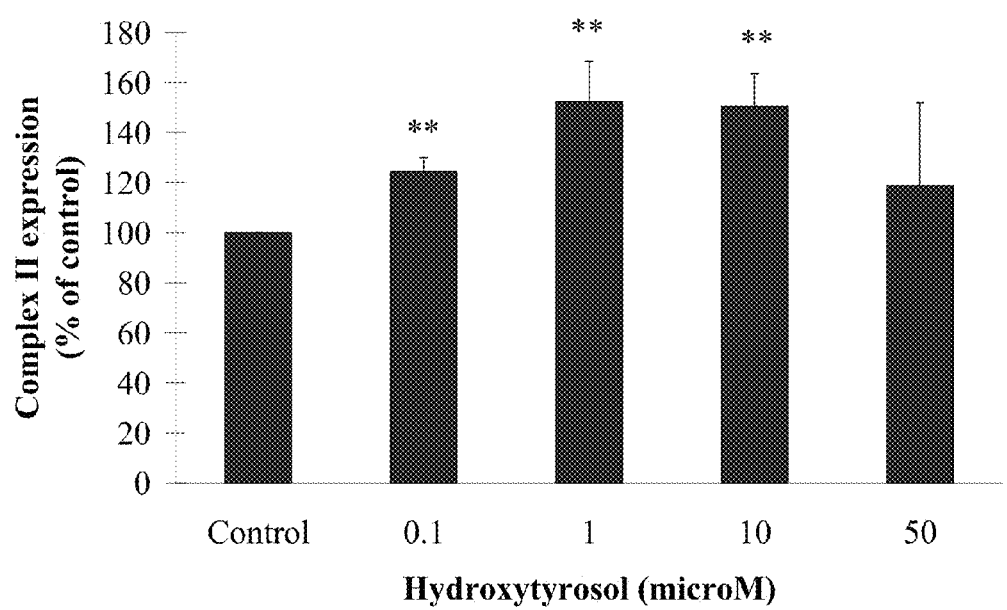
Figure 2C:
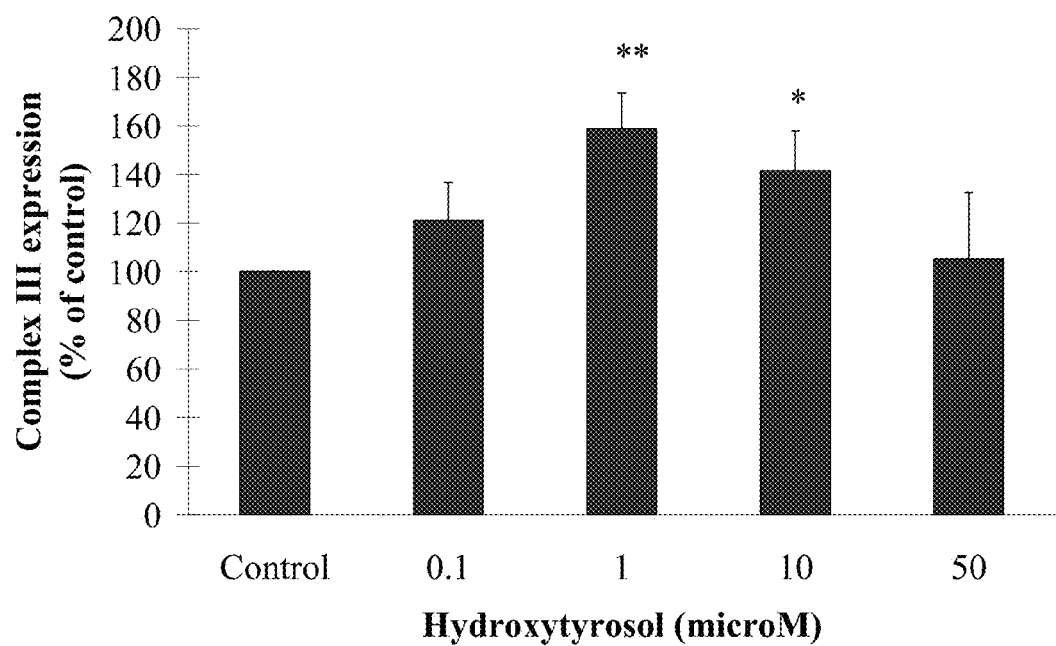
Figure 2D:
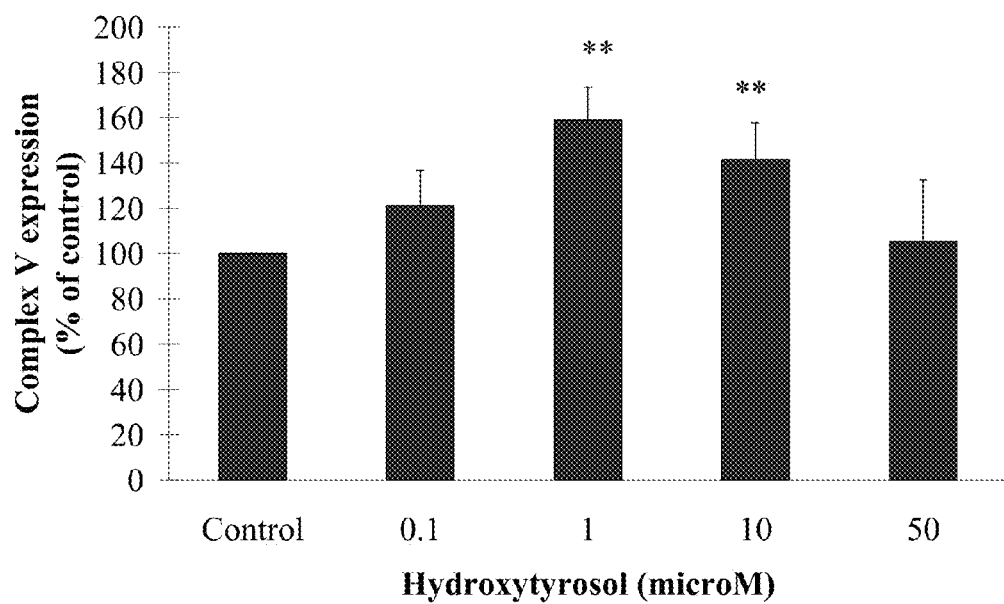

It has been found, in accordance with this invention, that hydroxytyrosol ("HT") in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract synergistically enhances the body's own energy metabolism by inducing mitochondrial biogenesis and can lead to an increased mitochondrial function in tissues.

Thus one aspect of this invention is a method of maintaining or increasing mitochondrial function and activity via increased mitochondrial biogenesis comprising administering to a mammal an effective amount of hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract and observing effects of mitochondrial function.

Mitochondrial biogenesis refers to processes of growth, amplification and healthy maintenance of the mitochondria. Mitochondrial biogenesis is a complex process involving both nuclear and mitochondrial players. Mitochondrial DNA encodes a small number of proteins, which are translated on mitochondrial ribosomes. Most of these proteins are highly hydrophobic subunits of the respiratory chain, which is localized in the inner mitochondrial membrane. Nuclear-encoded proteins are translated on cytosolic ribosomes and imported into mitochondria. These proteins include structural proteins, enzymes or enzyme subunits, components of the import-, replication-, transcription- and translation-machinery and chaperones.

Cells have to switch to the less efficient anaerobic energy metabolism, once the capacity for the aerobic respiration (electron chain) does not suffice anymore. It follows that increased mitochondrial biogenesis improves the capacity for aerobic energy metabolism, and thus increases the capacity for an efficient energy production.

"Mitochondrial biogenesis" as used throughout this specification and claims, includes all processes involved in maintenance and growth of the mitochondria, including those required for mitochondrial division and segregation during the cell cycle.

The use of the phrase "hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract" is intended to include the each single combination of hyroxytyrosol with each of the individual compounds within the group.

"Observing the effects of increased mitochondrial function" and "observing the effects of mitochondrial biogenesis" means either that the entity ingesting/applying the combination composition notices at least one of the effects listed below, or that a third party observer can notice or measure this effect.

Effects of increased mitochondrial function and/or mitochondrial biogenesis include observations that the combination of this invention:

helps promote endurance
helps promote recovery after exercise
helps reduce muscle fatigue
helps reduce muscle soreness
complements the immediate short term effect of caffeine with a sustained effect on energy generation
helps promote energy generation from fat
helps lower plasma lactate during exercise
helps maintain muscle force in conditions of oxidative stress
helps protect against exercise-induced oxidative stress helps the body to come up with more energy in a natural and sustained way—without caffeine and with only 1 calorie
helps the body to find more energy without getting too much caffeine.
gives long-lasting energy to sustain through your busy schedule.
helps boost body's own energy production in a natural sustained way.
helps you maintain more even energy levels throughout the day.
can in combination with caffeine provide for immediate and sustained energy
helps the body to adapt to exercise
helps prepare the body for your exercise goals
helps revamp your shape
facilitates the restart of your exercise program
helps you to get going again
helps you feeling more energetic
helps you feel more active
supports your zest for action
helps you cope with your busy lifestyle
Increased muscle work capacity
Improved aerobic capacity
Enhanced physical performance
Enhanced exercise performance
Improved running endurance, improved running distance and/or improved running time; or
Stimulate energy formation from nutrients As used throughout the specification and claims, the term "biogenesis-inducing amount" means that the overall mitochondrial biogenesis is at least maintained at the level which was present when the hydroxytyrosol was originally ingested. This can be determined in vitro by monitoring the amount and state of mitochondrial functioning in a tissue sample, or as described further in the Examples. Additionally, this can be determined in vivo by measuring the ATP content of tissue; or the oxygen consumption during exercise ($VO_2$ max), or ex vivo by transcriptomics analysis for upregulation of mitochondrial markers (such as Tfam), or by detecting the increased presence of mitochondrial DNA in tissue biopsies. This property of hydroxytyrosol is distinct from hydroxytyrosol's known activity as an antioxidant.

"Mitochondrial-stimulating" as used throughout this specification and claims means that the compound applied to the mitochondria leads to increased ATP production in the cell; an increased capacity for energy production in the cell; an increased capacity for aerobic energy generation or production in the cell; and/or an increased capacity for fat burning.

Hydroxytyrosol (3,4-dihydroxyphenylethanol) ("HT") may be of synthetic origin or it may be isolated or enriched from olive leaves, olive fruits, olive pulp, olive juice, or vegetation water of olive oil production. Thus, the term "hydroxytyrosol" also encompasses any material or extract of a plant or any material or extract of parts of a plant or any extract/concentrate/juice of fruits of a plant (such as olives) containing it or a precursor, especially in an amount of at least 1.5 weight %, preferably in an amount of at least 30 weight %, and more preferably in an amount of at least 40 weight-%, more preferably in an amount of at least 50, 55, 60, 65, 70, 75, 80, 85, 90 weight-%, and most preferably in an amount of at least 45 weight-%, based on the total weight of the plant material or extract. The commercial form of the extract may or may not be standardized to lower concentrations of hydroxytyrosol by formulating the hydroxytyrosol with suitable formulation exicipients. The terms "material of a plant" and "plant material" used in the context of the present invention means any part of a plant, also the fruits.

Precursors for hydroxytyrosol include complex polyphenols, which can be metabolized to hydroxytyrosol upon ingestion, such as oleuropein. It also includes tyrosol and tyrosol precursors and the like. Such polyphenols are well known and appreciated by those of skill in the art.

In further embodiments of the present invention, hydroxytyrosol derivatives such as esters and physiologically/pharmaceutically acceptable salts may be used instead of or in addition to hydroxytyrosol. It is also possible to use a mixture of hydroxytyrosol and hydroxytyrosol derivatives and precursors. Derivatives can be e.g. esters or glucosides, and are known to the person skilled in the art. Preferred esters of hydroxytyrosol are e.g. acetates or glucuronide conjugates; as well as oleuropein being the most preferred one.

Thus, one aspect of this invention is the use of hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract.

In a preferred embodiment, the hydroxytyrosol is used in combination with at least one of the compounds selected from the group consisting of: creatine, coenzyme Q10, resveratrol, caffeine, carnitine, B vitamins (B1, B2, B3, B5, B6, and/or B12) and ginseng extract in the manufacture of a medicament or food product (for humans and/or animals) which is useful for maintaining or increasing mitochondrial biogenesis or mitochondrial function.

In yet another embodiment, the hydroxytyrosol is used in combination at least one of the compounds selected from the group consisting of: caffeine, carnitine, and a B vitamin.

Another aspect of this invention is a method of maintaining or increasing mitochondrial biogenesis in a subject in need thereof comprising administering a mitochondrial biogenesis-inducing or mitochondrial-stimulating amount of hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract and observing the effects of mitochondrial biogenesis.

Another aspect of this invention is the use of hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract in the manufacture of a medicament or food product (for humans and/or for animals) which is useful in protecting mitochondria against any number of stresses found in the daily environment.

Examples of stresses found in the daily environment include UV(A) light, infections, exposure to environmental pollution, inflammation, and chronic degenerative diseases. Thus, these products help to ensure normal mitochondrial function in the face of everyday insults, such as cellular biochemical changes as a result of stresses, illnesses, malnutrition (including malnutrition which is secondary to another disease state) or injury.

Another aspect of this invention are nutraceuticals which comprise a mitochondrial biogenesis-inducing amount of hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract, and which promote mitochondria well-being and encourage optimal mitochondrial function.

Another aspect of this invention is a cosmetic composition which comprises a mitochondrial biogenesis-inducing amount of hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract, and which promotes mitochondria well-being and which encourages optimal mitochondrial function in the skin, and thus which boosts the energy metabolism of the skin.

PGC1α, Peroxisome proliferation activator receptor (PPAR) gamma-coactivator 1 alpha, a transcription coactivator, functions as a master regulator of a wide array of metabolic and physiological processes and is an essential factor in the process of mitochondrial biogenesis. PGC-1α overexpression stimulates mitochondrial biogenesis in 3T3 cells making them more resistant to oxidative stressors.

The inventors have demonstrated that hydroxytyrosol at 1.0-10 µM, increases PGC1α protein level and promotes mitochondrial biogenesis. Creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract will synergistically increase mitochondrial activity and prevent mitochondrial dysfunction in different tissues. Further, hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract, can thus maintain tissue/organ function and prevent tissue/organ failure triggered by mitochondrial dysfunction.

A further aspect of this invention are compositions comprising a mitochondrial biogenesis-inducing amount of hydroxytyrosol and at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract for synergistically enhancing the body's own energy metabolism by synergizing with one or more of the ingredients (in the case of resveratrol, CoQ10, creatine, B vitamins, and ginseng extract), or by synergistically promoting fat burning (in the case of carnitine).

If ginseng extract is used in combination with hydroxytyrosol, it is preferably in the form of ginseng root extract.

Preferred combinations of this invention include:
  HT and resveratrol, quercetin, alpha-lipoic acid or EGCG for further increase in mitochondrial biogenesis and mitochondrial function, leading to a synergistic increase of mitochondrial capacity for aerobic energy generation.
  HT and CoQ10 and/or vitamin B2: HT increases mitochondrial mass, and these newly synthesized mitochondria need to be staffed with CoQ10 and B2. This results in a synergistic production of more ATP (energy).
  For making more ATP and making it available for the body (physical energy, endurance, muscle force) either HT and creatine or HT, CoQ10 and/or B2 and creatine are preferred. HT increases mitochondrial mass, and these newly synthesized mitochondria need to be staffed with CoQ10 and B2. Creatine transports the energy generated in form of ATP to the myofibers in usable form (creatine phosphate)
  For improving body composition (fat:muscle ratio): HT and carnitine. Carnitine aids in the transport of fatty acid into mitochondria for fat burning and ATP production. HT surprisingly was found to upregulate CPT-1 (carnitine palmitoyl transferase 1), the transporter, which employs carnitine employs for the fatty acid transport. CPT-1 is the gatekeeper of mitochondrial fatty acid oxidation because it regulates long-chain fatty acid transport across the mitochondrial membrane by converting acyl-CoA into acylcarnitine. Furthermore, we surprisingly found a synergistic elevation of the mitochondrial membrane potentioal by a combination of hydroxytyrosol and carnitine.
  For immediate and sustained energy, HT and caffeine is preferred. Preferred dosages are 10-200 mg HT and 50-450 mg caffeine. Furthermore, we suprisingly found a synergistic elevation of the mitochondrial membrane potential by a combination of hydroxytyrosol and caffeine.

Another aspect of this invention is HT in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract as an active ingredient in "better for you energy products" such as energy drinks, snacks including chocolate, biscuits, or bars.

Another aspect of this invention is HT in combination with caffeine in reduced caffeine doses for people who would like to have sufficient energy for their lifestyle, but want to cut on their caffeine intake.

Mitochondrial function, thus available energy, decreases with aging. Thus, another preferred embodiment of the invention is also energy products comprising HT in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract, formulated for people aged over 50, looking to maintain a youthful energy level, so as to maintain an active lifestyle.

Physical Performance & Adaptation to Exercise

An increase in mitochondria can benefit both people and animals involved in exercise. Mitochondria biogenesis translates into increase oxygen usage and increased energy while engaging in any form of exercise. Higher mitochondrial volumes improve the capacity for oxidative metabolism at high glycolytic flux rates. Further, this results in increased endurance. The muscle fibers, which have access to greater energy stores are able to contract faster and more fully; thus improvements in speed and strength can be seen after usages over a period of time.

Additionally, improved fatty acid oxidation capacity results in decreased glucose utilization at submaximal exercise intensities. Moreover, fat metabolism proceeds via a different pathway than glucose, and lactic acid is not produced. Also, recovery times from injury, cramps, and soreness resulting from anaerobic energy production will be quicker.

In another muscular application, muscles which utilize energy more efficiently are less prone to fat buildup, and thereofore, hydroxytyrosol and a compound selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract can be used to improve body-shaping.

Veterinary applications of the mitochondrial biogenesis inducing amount of hydroxytyrosol and a compound selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract include: to increase performance in race animals, such as race horses and dogs, and racing camels; to increase endurance in draft animals.

Regular physical exercise also induces mitochondria as an adaptation to the sudden surge in energy demand during exercise. The claimed synergistic combinations can help prepare/adapt the body for exercise beyond the habitual exercise levels. This is of interest predominantly in people who start exercising (again) after a longer break (e.g. several days, weeks, months, years) of regular exercise, who therefore feel sluggish, week, slow, tired and fatigued when trying to (re)start their exercise regimen. It also is of interest to lifestyle athletes (recreationally active people, weekend warriors), who do not have the time for sufficient exercise to prepare for their weekend tours or races/competitions.

Feeling Energetic

In addition to improving physical performance in exercising people, the combination of this invention can help to generate the energy needed for today's lifestyles. Consumer research showed that 37% of respondents (general population, Age 16+, US and 4 European countries) often felt tired or lacked energy. A second study found that 60% of respondents would be interested in products helping to have more energy. Today, people in need of an energy boost, consume coffee or caffeine-containing energy beverages, as well as high sugar, high fat snacks.

If consumed at the right dose, the immediate effect of caffeine to relieve tiredness is much appreciated. However, if overconsumed, it can cause sleeplessness and hypertension. A typical cup of coffee can contain approximately 100 mg caffeine. If a person regularly drinks 3-5 cups per day, the caffeine consumption can be quite high (+300 mg per day). Hydroxytyrosol, due to its stimulating effect on mitochondrial biogenesis, can add a long term effect of sustained energy to the short term immediate effect of caffeine.

Moreover, hydroxytyrosol can over time help reduce the caffeine dose needed to cope with the day's duties. With the addition of hydroxytyrosol to the diet, the same non-lethargic feeling can be achieved, but the amount of caffeine needed is reduced (to 100 mg or less per day).

Similarly, consumers often eat foods high in sugars and/or fat to provide an energy boost. However, with the sustained energy increase from hydroxytyrosol and a compound selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract, the amount required is reduced. Thus, the HT combinations of this invention can favourably be used in "better for you" (BFY) energy offers (drinks, bars, snacks, gums, shots, supplements and the like) with a lower content in calories from sugar or fat, or in caffeine.

Thus present invention is directed to the use of the hydroxytyrosol-containing combinations for
increasing body's own capacity for energy generation
increasing the aerobic capacity for exercise
shifting nutrient usage for energy generation from carbohydrate to fat burning
complementing the immediate short term effect of caffeine with a sustained effect on energy generation
allowing one to reduce the caffeine and/or sugar and/or fat dose needed to "keep going".

Thus, another aspect of this invention is a composition comprising hydroxytyrosol and a compound selected from the group consisting of creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract to maintain or increase mitochondrial biogenesis, wherein the maintained or increased mitochondrial biogenesis results in a sustained energy boost. A further aspect of this invention is a method of making a food composition which provides energy or alertness enhancement comprising adding a hydroxytyrosol combination according to this invention. Yet another aspect of this invention is a method of making a food composition which provides energy or alertness enhancement comprising hydroxytyrosol and a compound selected from the group consisting of creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract, wherein the food composition contains a reduced caffeine, fat, and/or sugar content compared to a similar food item which does not contain hydroxytyrosol.

Improve Muscle/Fat Ratio, Body Shaping

The present invention is directed to the use of hydroxytyrosol and a compound selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract for
- increasing muscle metabolism to boost energy mobilization;
- improving skeletal muscle mass by stimulating anabolic pathways, inhibiting catabolic pathways and accelerating muscle regeneration when damaged;
- shifting nutrient usage for energy generation from carbohydrate or protein burning to fat burning;
- promoting fat burning; acting as a regulator of fat burning, increasing energy expenditure by fatty acid oxidation, increasing fat metabolism, promoting fat oxidation, decreasing body fat and increasing muscle mass;
- helping to achieve a good silhouette (body shaping), decreasing body fat and increasing lean muscle mass; and
- increasing thermogenesis; increasing the metabolism of a human or animal to burn more energy;

Formulations

Hydroxytyrosol or olive juice extracts containing hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract according to the present invention can be used in any suitable form such as a food, or a beverage, as Food for Special Nutritional Uses, as a dietary supplement, as a nutraceutical or in animal feed or food.

The hydroxytyrosol or olive juice extracts containing hydroxytyrosol in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract may be added at any stage during the normal process of these products. Suitable food products include e.g. cereal bars, bakery items such as cakes and cookies or other types of snacks such as chocolate, nuts, gummy bears, chewing gums, and the like, and also liquid foods such as soups or soup powders. Suitable beverages encompass non-alcoholic and alcoholic drinks as well as liquid preparations to be added to drinking water and liquid food. Non-alcoholic drinks are preferably mineral water, sport drinks, energy drinks including those containing glucuronolactone for increased mental alertness and taurine for detoxification, hybrid energy drinks, near water drinks, fruit juices, lemonades, smoothies, teas and concentrated drinks such as shots and mini-shots. The sports drinks can be hypotonic, hypertonic or isotonic. Sports drinks can be available in liquid form, as concentrates or as powder (to be dissolved in a liquid, as for example water). Examples of Foods for Special Nutritional Uses include the categories of sport food, slimming foods, infant formula and clinical foods. Feed includes any animal food or feed premix, including items such as pet treats and snacks.

The term "dietary supplement" as used herein denotes a product taken by mouth that contains a compound or mixture of compounds intended to supplement the diet. The compound or mixture of compounds in these products may include: vitamins, minerals, herbs or other botanicals and amino acids. Dietary supplements can also be extracts or concentrates, and may be found in many forms such as tablets, capsules, softgels, gelcaps, liquids, or powders. The dietary supplement can also be used to promote energy to the dermal mitochondria, thus enhancing esthetic qualities of the skin.

The term "nutraceutical" as used herein denotes the usefulness in both the nutritional and pharmaceutical field of application. The nutraceutical compositions according to the present invention may be in any form that is suitable for administrating to the animal body including the human body, especially in any form that is conventional for oral administration, e.g. in solid form such as (additives/supplements for) food or feed, food or feed premix, tablets, pills, granules, dragées, capsules, and effervescent formulations such as powders and tablets, or in liquid form such as solutions, emulsions or suspensions as e.g. beverages, pastes and oily suspensions. Controlled (delayed) release formulations incorporating the hydroxytyrosol or olive juice extracts containing hydroxytyrosol according to the invention also form part of the invention. Furthermore, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns. The nutraceutical can further comprise usual additives, for example sweeteners, flavors, sugar, fat, emulgators, preservatives. The nutrition can also comprise other active components, such as (hydrolysed) proteins as described in for example WO 02/45524. Also anti-oxidants can be present in the nutrition, for example flavonoids, carotenoids, ubiquinones, rutin, lipoic acid, catalase, glutathione (GSH) and vitamins, such as for example C and E or their precursors.

In a further embodiment, a hydroxytyrosol containing composition in combination with at least one of the compounds selected from the group consisting of: creatine, coenzyme Q10, resveratrol, caffeine, carnitine, B vitamins (B1 or thiamine; B2 or riboflavin; B3 or niacin or niacinamide; B5 or pantothenic acid; B6 or pyridoxine, pyridoxal, pyridoxamine, or pyridoxine hydrochloride; B7 or biotin; B9 or folic acid; or B12 or various cobalamins, such as cyanocobalamin), quercetin, alpha-lipoic acid, EGCG and ginseng extract is applied topically in order to enhance the mitochondrial biogenesis of dermal cells. The cosmetic or dermatological preparations according to the invention may be in the form of a suspension or dispersion in solvents or fatty substances, or alternatively in the form of an emulsion or micro emulsion (in particular of O/W or W/O type, O/W/O or W/O/W-type, wherein O stands for oil phase and wherein W stands for water phase), such as a cream, a paste, a lotion, a thickened lotion or a milk, a vesicular dispersion in the form of an ointment, a gel, a solid tube stick or an aerosol mousse, and may be provided in the form of a mousse, foam or a spray foams, sprays, sticks or aerosols or wipes. Examples of cosmetic or dermatological preparations are skin care preparations, in particular, body oils, body lotions, body gels, treatment creams, skin protection ointments, moisturizing gels, moisturizing sprays, revitalizing body sprays, after sun preparations or sunscreen formulations.

The cosmetic or dermatological preparations of the invention may further comprise the usual cosmetic respectively dermatological adjuvants and/or additives such as preservatives/antioxidants, fatty substances/oils, water, organic solvents, silicones, thickeners, softeners, emulsifiers, additional light screening agents, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, light stabilizers, insect repellants, skin tanning agents, skin whitening agents, antibacterial agents, preservatives active ingredients or any other ingredients usually formulated into cosmetics.

Generally between about 1 mg to about 500 mg of hydroxytyrosol in the pure form or in an olive extract is effective per serving. Preferably between 1 mg and 250 mg hydroxytyrosol is present in the pure form or in the olive extract, and even more preferably between about 1 mg and 100 mg in an olive extract is used The daily dosage of hydroxytyrosol for humans (70 kg person) may be at least 0.1 mg. It may vary from 1 to 500 mg, preferably from 5 to 100 mg.

The preferred dose of hydroxytyrosol varies from 0.28 to 1.9 mg/kg metabolic body weight for mammals, whereby "metabolic body weight" [in kg]=(body weight [in kg])$^{0.75}$ for mammals. That means e.g. that for a human of 70 kg the preferred daily dose would vary between 6.77 and 45.98 mg, for a 20 kg dog the preferred daily dose would vary between 2.23 and 15.1 mg.

Resveratrol doses typically range from 1 mg-450 mg/d per human. The resveratrol may be made synthetically using known processes or extracted from plants including Giant knotweed.

CoQ10 may be purchased from Kaneka, USA. Preferred dosages are 3-100 mg per day per person, and more preferred is 30-50 mg.

Creatine dosages preferably range from 1 g-25 g per day per person. It is commercially available.

Carnitine dosages typically range from 250 mg-1 g per day per person. It is commercially available as "CARNIPURE" from Lonza.

Caffeine dosages are typically from 6 mg-450 mg per day per person. It is commercially available.

Ginseng dosages are preferably 100 mg-5 g dried root powder or extract with corresponding ginsenoside content per day per person.

RDAs/DRIs (recommended dietary allowance/Daily recommended intakes of various B vitamins are known. Preferred vitamin doses in accordance with this invention range from 10% to 1000% of the DRI (Daily recommended intake)/RDA (recommended dietary allowance) as currently recommended in US or Europe.

Preferred vitamin doses are as follows:

Thiamin dosages are typically from 0.1-10 mg per day per person. It is commercially available.

Riboflavin dosages are typically from 0.1-10 mg per day per person. It is commercially available.

Niacin dosages are typically from 1-200 mg per day per person. It is commercially available.

Pantothenic acid dosages are typically from 1-100 mg per day per person. It is commercially available.

Vitamin B6 (such as Pyridoxin, pyridoxal, or pyridoxamine) dosages are typically from 0.1-20 mg per day per person. It is commercially available.

Biotin dosages are typically from 0.1-20 mg per day per person. It is commercially available.

Cobalamine dosages are typically from 0.1-20 microg per day per person. It is commercially available.

Quercetin dosages are typically from 50 mg to 2000 mg per day per person as plant extract eg from apples (e.g. peel), onions (e.g. peel), or tea leaves. It is commercially available.

Alpha-lipoic acid dosages are typically from 200 mg-1800 mg per day per person. It is commercially available.

EGCG (epigallocatechin) dosages are typically from 25 mg-600 mg EGCG per day per person as green tea extract. It is commercially available.

The following non-limiting Examples are presented to better illustrate the invention.

EXAMPLES

Example 1

Anti-rabbit PGC-1α and anti-rabbit PPAR-γ were purchased from Santa Cruz (Calif., USA); anti-α-tubulin from Sigma (St. Louis, Mo., USA); Mito-Tracker Green FM, anti-oxidative complex I, II, III, and V from Invitrogen (Carlsbad, USA); SYBR® GREEN PCR Master Mix from ABI (Warrington, UK); BD Oxygen Biosensor System plate from BD Biosciences (California, USA); Hydroxytyrosol (DSM Nutritional Products); Mitochondrial D-loop and 18SRNA primers were synthesized by Bioasia Biotech (Shanghai, China), other reagents for cell culture were from Invitrogen (Carlsbad, USA).

Cell Culture and Adipocyte Differentiation

Murine 3T3-L1 pre-adipocytes (American Type Culture Collection) were cultured in Dulbecco's Modified Eagle's Medium (DMEM) supplemented with 10% fetal bovine serum and allowed to reach confluence. Differentiation of pre-adipocytes was initiated with 1 μM insulin, 0.25 μM dexamethasone and 0.5 mM 3-isobutyl-1-methylxanthine in DMEM, supplemented with 10% fetal bovine serum. After 48 h, the culture medium was replaced with DMEM supplemented with 10% fetal bovine serum and 1 μM insulin. The culture medium was changed every other day with DMEM containing 10% fetal bovine serum. Cells were used 9-10 days following differentiation induction when exhibiting 90% adipocyte phenotype.

Determination of Mitochondrial Mass

Adipocytes were trypsinized and centrifuged at 1,000 rpm at 4° C. for 5 min, resuspended in Kreb's Ringer solution buffered with HEPES and 0.1% BSA, then incubated with 0.1 μM MitoTracker Green FM in DMEM for 30 min at 37° C. Cells were centrifuged at 1,000 rpm at 4° C. for 5 min and resuspended in 400 μl of fresh Kreb's Ringer solution buffered with HEPES. To examine relative mitochondrial staining in the fractions, 20×10$^3$ Mitotracker-labeled cells in 200 μl PBS from each fraction were loaded into a 96-well plate and relative fluorescence intensity was read (excitation 485±25 nm; emission 538±25 nm) using a fluorescence microplate spectrophotometer (Molecular probe). Results are expressed as fold increase of the fluorescence intensity over untreated control cells. Values are mean±SE of the results from four independent experiments.

Western Blot Analysis

After treatment, cells were washed twice with ice-cold PBS, lysed in sample buffer (62.5 mM Tris-Cl pH 6.8, 2% SDS, 5 mM DTT) at room temperature and vortexed. Cell lysates were then boiled for 5 minutes and cleared by centrifugation (13,000 rpm, 10 minutes at 4° C.). Protein concentration was determined using the Bio-Rad DC protein assay. The soluble lysates (10 µg per lane) were subjected to 10% SDS-PAGE, proteins were then transferred to nitrocellulose membranes and blocked with 5% non-fat milk/TBST for 1 h at room temperature. Membranes were incubated with primary antibodies directed against PPAR-γ (1:1000), PGC-1α (1:1000), α-tubulin (1:10 000), Complex I (1:2000), Complex II (1:2000), Complex III (1:2000) and Complex V (1:2000) in 5% milk/TBST at 4° C. overnight. After washing membranes with TBST three times, membranes were incubated with horseradish peroxidase-conjugated secondary antibody for 1 h at room temperature. Western blots were developed using ECL (Roche Manheim, Germany) and quantified by scanning densitometry.

Measurement of Respiration in Adipocytes

Oxygen consumption by intact cells was measured as an indication of mitochondrial respiration activity. The BD™ Oxygen Biosensor System (BD Biosciences, Franklin Lakes, N.J., USA) is an oxygen sensitive fluorescent compound (tris 1,7-diphenyl-1,10 phenanthroline ruthenium (II) chloride) embedded in a gas permeable and hydrophobic matrix permanently attached to the bottom of a multiwell plate. The concentration of oxygen in the vicinity of the dye is in equilibrium with that in the liquid media. Oxygen quenches the dye in a predictable concentration dependent manner. The amount of fluorescence correlates directly to the rate of oxygen consumption in the well, which in turn can relate to any sort of reaction that can be linked to oxygen consumption. The unique technology allows homogenous instantaneous detection of oxygen levels. After treatment, adipocytes were washed in KRH buffer plus 1% BSA. Cells from each condition were divided into aliquots in a BD Oxygen Biosensor System plate (BD Biosciences) in triplicate. Plates were sealed and "read" on a Fluorescence spectrometer (Molecular probes) at 1-minute intervals for 60 minutes at an excitation wavelength of 485 nm and emission wavelength of 630 nm. The number of cells contained in equal volumes was not statistically significantly between conditions (Wilson-Fritch et al., 2004 *J Clin Invest* 114: 1281-1289).

Measurement of Mitochondrial DNA

Quantitative PCR was performed in Mx3000P Real-Time PCR system Stratagene). Reactions were performed with 12.5 µl SYBR-Green Master Mix (ABI), 0.5 µl of each primer (10 µM), 100 ng template (DNA) or no template (NTC), and Rnase-free water was added to a final volume of 25 µl. The cycling conditions were as follows: 50° C. for 2 min, initial denaturation at 95° C. for 10 min, followed by 40 cycles of 95° C. for 30 sec, 55° C. for 1 min and 72° C. for 30 sec. Each quantitative PCR was performed in triplicate. The following primers were used: mitochondrial D-loop forward, mitochondrial D-loop reverse, 18SRNA forward, and 18SRNA reverse. The mouse 18S rRNA gene served as the endogenous reference gene. The melting curve was done to ensure specific amplification. The standard curve method was used for relative quantification. The ratio of mitochondrial D-loop to 18S rRNA was then calculated. Final results are presented as percentage of control.

Assays for Activities of Mitochondrial Complex I, II, and III

Adipocytes were cultured in 100 mm plates, washed in PBS, resuspended in an appropriate isotonic buffer (0.25 M sucrose, 5 mM Tris-HCl, pH 7.5, and 0.1 mM phenylmethylsulfonyl fluoride), and homogenized. Mitochondria were isolated by differential centrifugation of the cell homogenates. NADH-CoQ oxidoreductase (Complex I), succinate-CoQ oxidoreductase (complex II), CoQ-cytochrome c reductase (complex III) were assayed spectrometrically using the conventional assays (Picklo and Montine, 2001 *Biochim Biophys Acta* 1535: 145-152; Humphries, K. M., and Szweda, L. I. 1998 *Biochemistry* 37:15835-15841), with minor modifications Assays for Analysing Expression of Cpt1α mRNA.

3T3-L1. Adipocytes were treated for 48 hrs with HT at 0.1, 1.0, 10, and 50 µmol/l, and total RNA was isolated. Cpt1a expression was analysed by RT-PCR using the conditions described in in Shen W, Liu K, Tian C, et al. R-alpha-Lipoic acid and acetyl-L: -carnitine complementarily promote mitochondrial biogenesis in murine 3T3-L1 adipocytes. *Diabetologia* 2008; 51:165-174.

The cycle number at which the various transcripts were detectable was compared with that of 18S rRNA as an internal control.

Statistical Analysis

All qualitative data were representative of at least three independent experiments. Data are presented as means±SE. Statistical significance was determined by using one-way ANOVA with Bonferroni's post hoc tests between the two groups. The criterion for significance was set at p<0.05.

Results:

Effect of Hydroxytyrosol on PGC-1α Protein Level in Adipocytes

As shown in FIG. 1, hydroxytyrosol showed a bell-shape effect on increasing PGC-1α from 0.1 to 10.0 µM with a maximum protein expression at 1.0 µM (205±52%, p, 0.05 vs. control).

Effect of Hydroxytyrosol on Complex I, II, III and V Protein Expression in Adipocytes Mitochondrial complexes was determined by western blot (FIG. 2 A to D). An increase on mitochondrial electron transport complex I protein was observed with hydroxytyrosol treatment at 0.1 µM (131±16%, p<0.05 vs. control), 1.0 µM (163±31%, p<0.01 vs. control) and 10.0 µM (138±21%, p<0.05 vs. control) (Figure A). Complex II protein expression was also significantly increased with hydroxytyrosol at 0.1, 1.0 and 10.0 µM (Figure B). Complex III and V protein expression was significantly increased with hydroxytyrosol at 0.1, 1.0 and 10.0 µM (Figure C and D).

Effects of Hydroxytyrosol on Mitochondrial DNA

Figure 3:
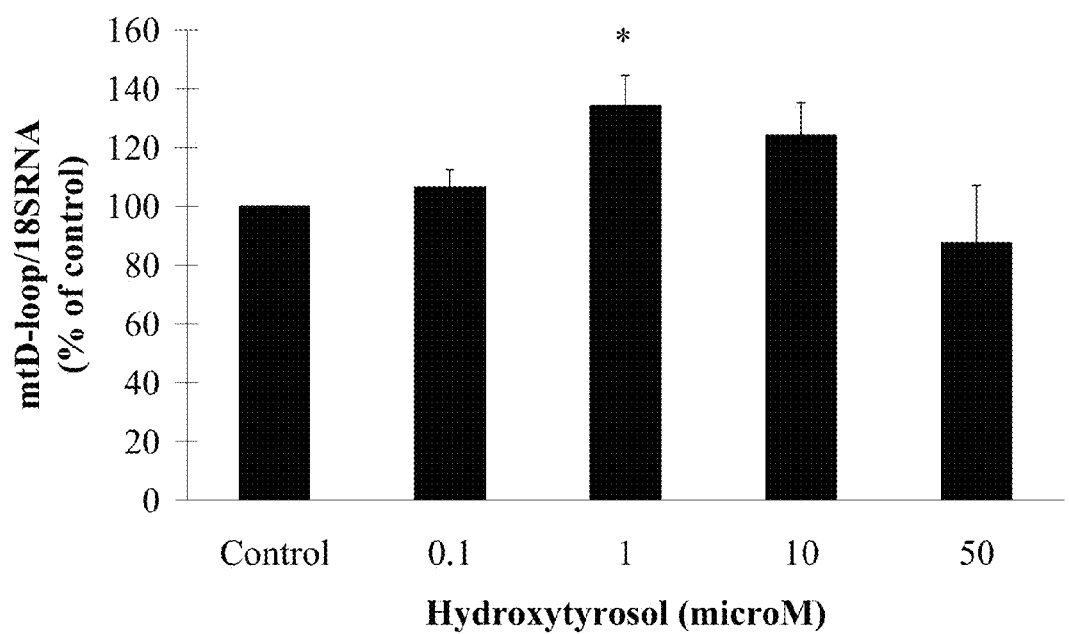
FIG. 3 shows expression of mitochondrial DNA. 3T3-L1 adipocytes were treated for 48 hrs with hydroxytyrosol. PCR products were quantified by fluorescence using SYBR Green. Quantitative values tabulated for D-loop:18sRNA ratio. Results are expressed as % of control. Data are mean±SE (n=5). *$P<0.05$ vs. control; ** $p<0.01$ vs. control.

As the D-loop is known as the major site of transcription initiation on both the heavy and light strands of mtDNA, we examined in vitro whether hydroxytyrosol could increase mtDNA expression. As shown in FIG. 3, the ratio of mt D-loop/18SRNA was significantly increased in adipocytes treated with hydroxytyrosol at 1.0 µM.

Effect of Hydroxytyrosol on Oxygen Consumption in Adipocytes

Figure 4:
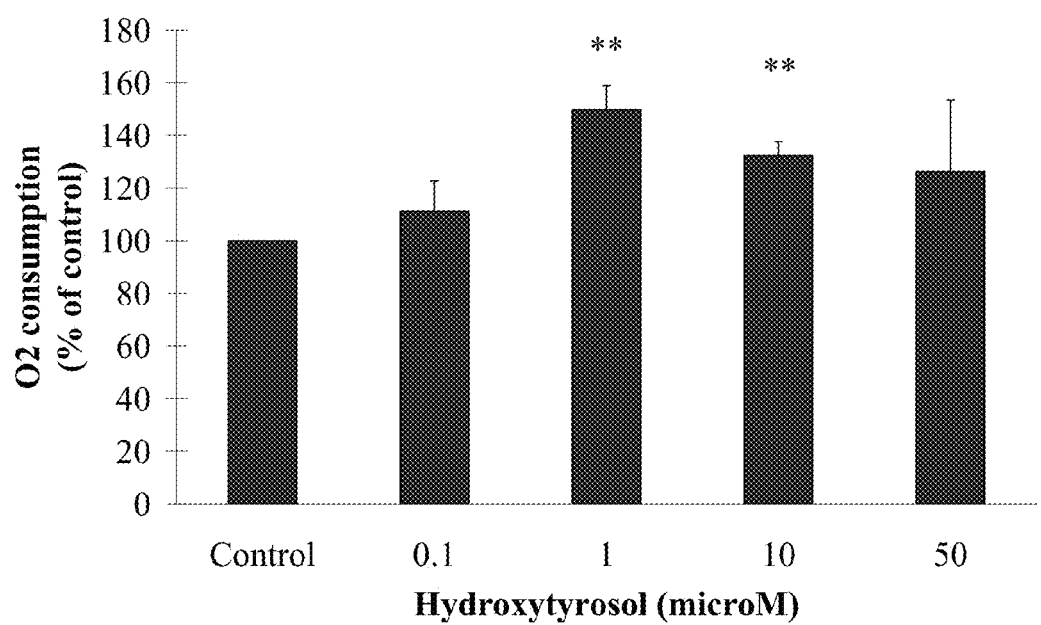
FIG. 4 shows oxygen consumption in 3T3-L1 adipocytes. Equal volumes of cells were separated into aliquots in wells of a 96-well BD Oxygen Biosensor plate. Plates were covered and fluorescence in each well was recorded over time with a fluorescence microplate spectrophotometer. Quantitative changes in the respiratory rate of adipocytes during each condition were calculated by determining the kinetic measurements. Values are mean±SE; results shown are % of control from 3 independent experiments compared with control cells. *p<0.05 vs. control.

To determine whether increased mitochondrial biogenesis is accompanied by changes in oxygen consumption, cells were treated with hydroxytyrosol at 0.1, 1.0, 10 and 50 µM. As shown in FIG. 4, the basal rate of oxygen consumption was significantly increased in adipocytes treated with hydroxytyrosol at 1.0-10.0 µM.

Figure 5A:
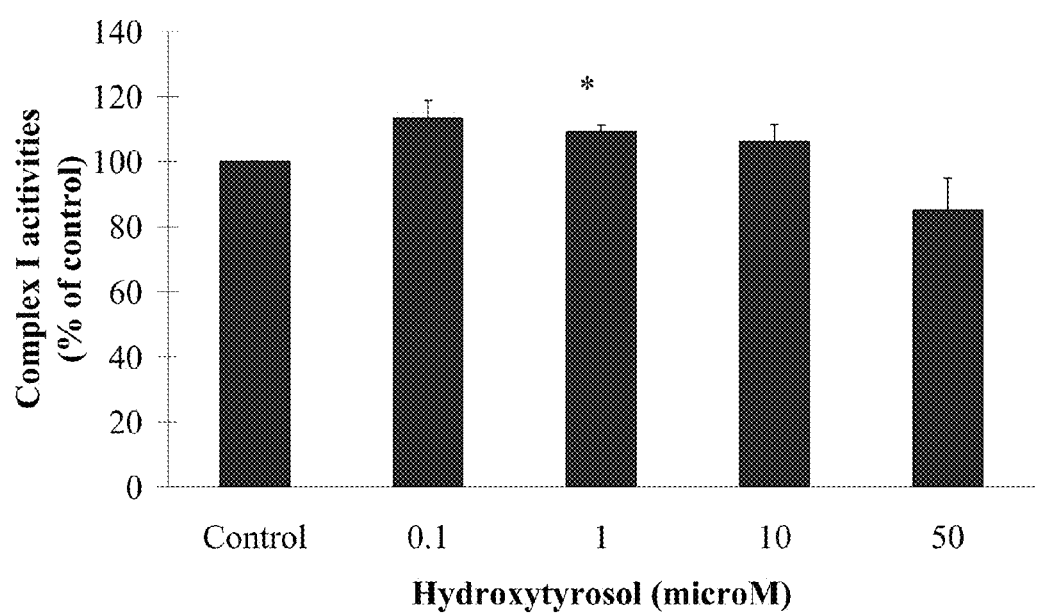
Figure 5B:
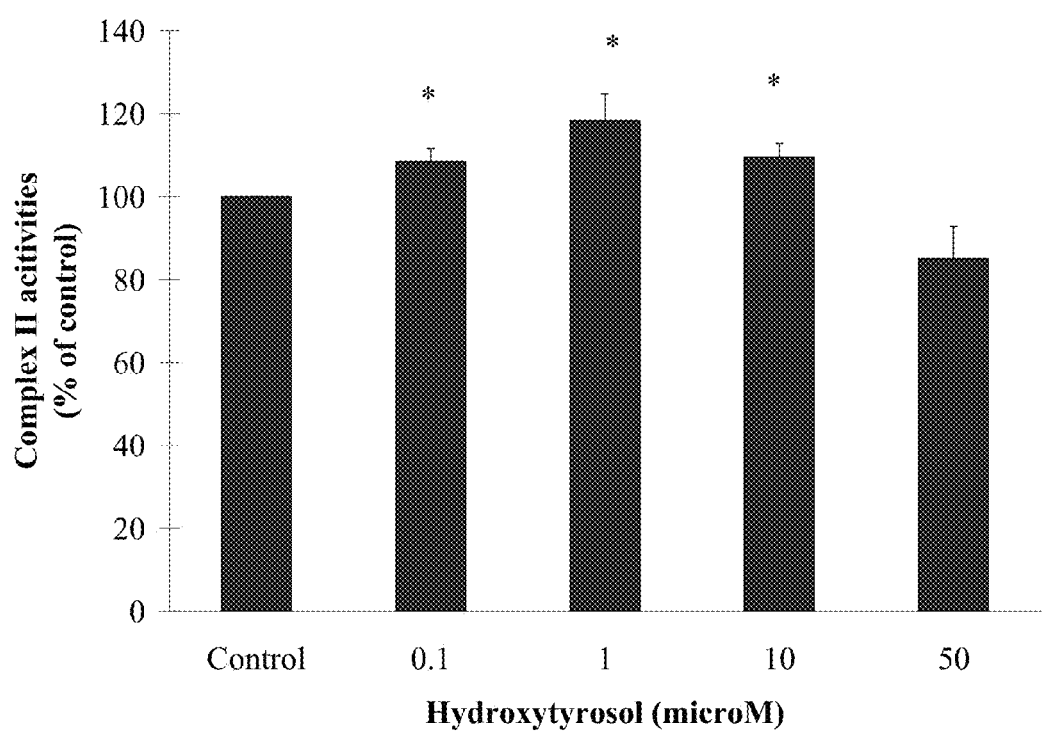
Figure 5C:
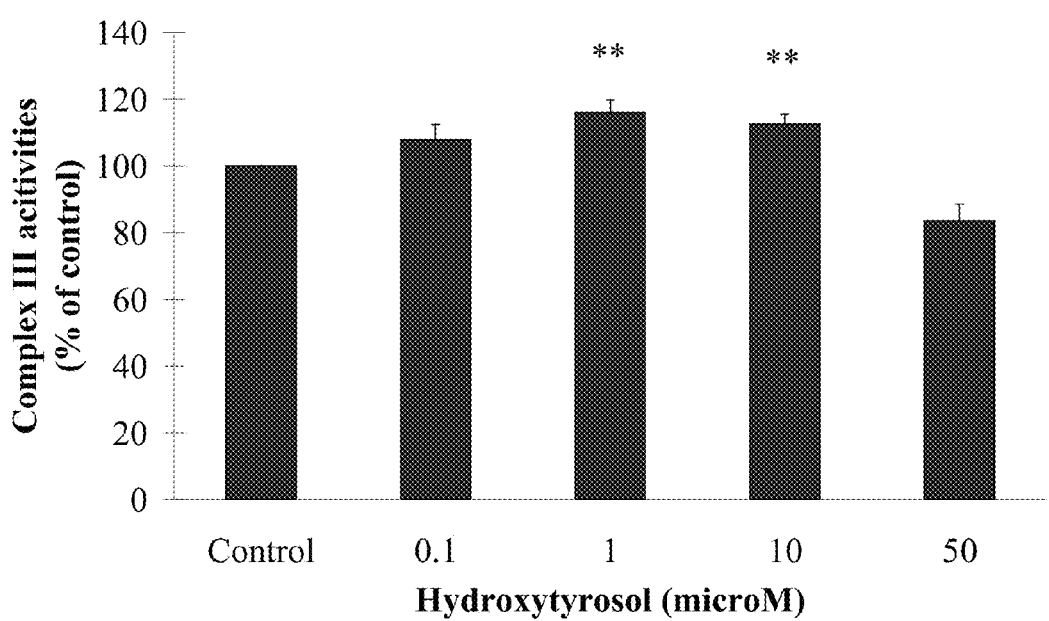
Figure 5D:
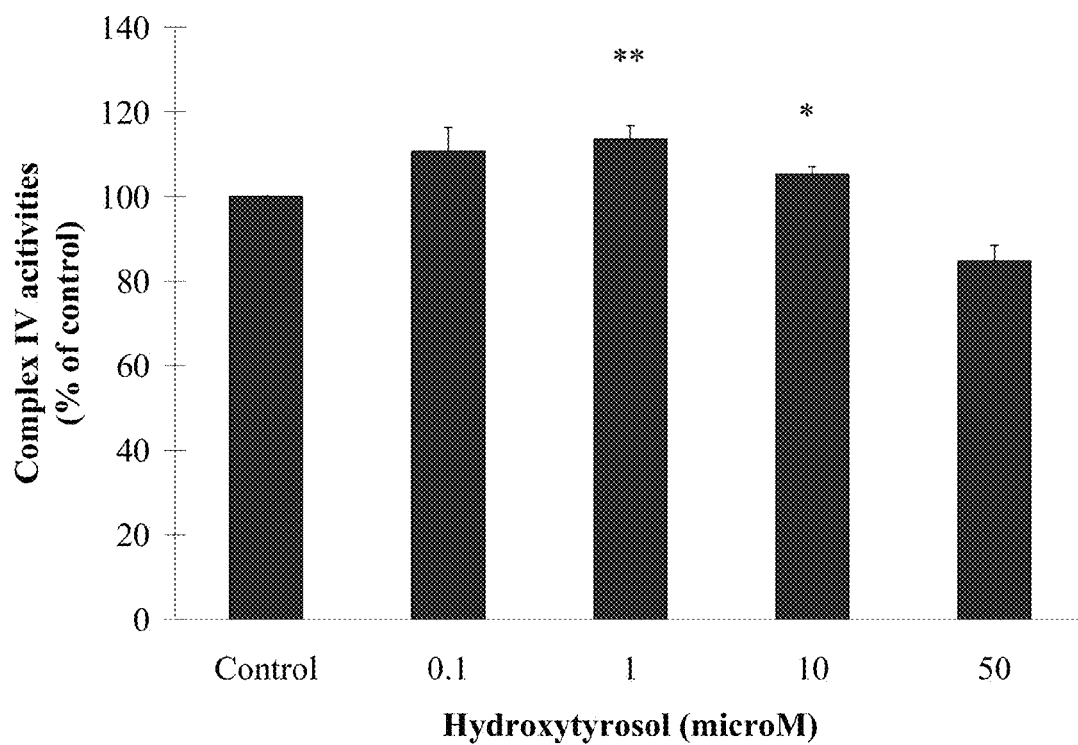
Figure 6:
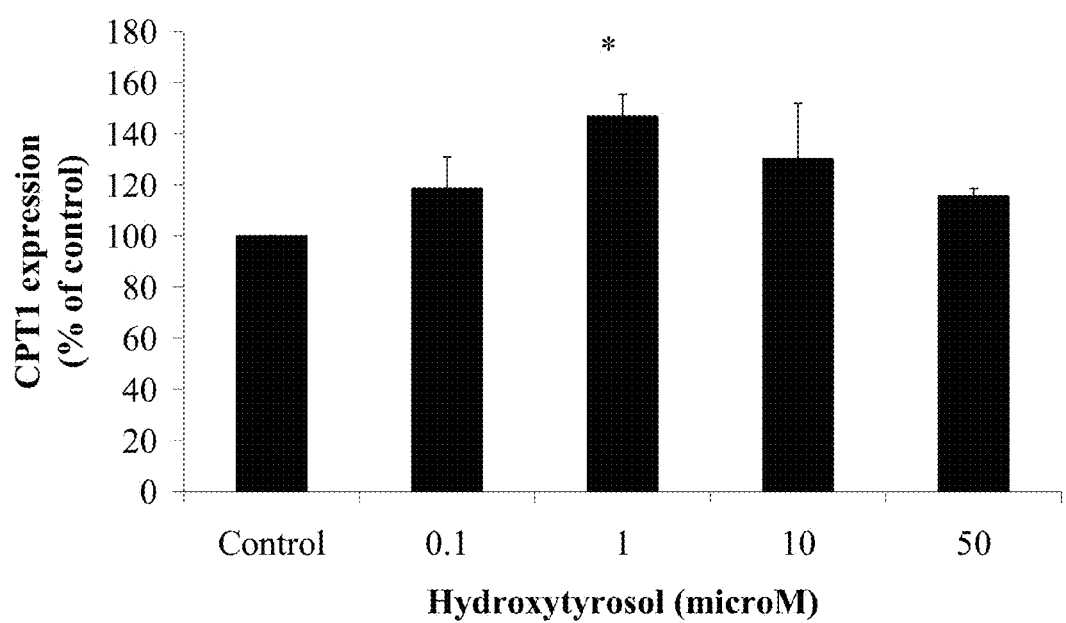
FIG. 6 Effect of HT treatments on expression of Cpt1a mRNA. 3T3-L1. Adipocytes were treated for 48 hrs with HT at 0.1, 1.0, 10, and 50 µmol/l, and total RNA was isolated. The cycle number at which the various transcripts were detectable was compared with that of 18S rRNA as an internal control. Results are expressed as % of control. Values are mean±SE of the results from at least four independent experiments. *P<0.05 vs. control without HT treatment.

Effect of Hydroxytyrosol on Activities of Mitochondrial Complex I, II, III, IV and V Hydroxytyrosol showed significant increase in the activity of mitochondrial complex I in adipocytes cells at 1.0 µM respectively relative to control (FIG. 5A). The activity of mitochondrial complex II was significantly increased with hydroxytyrosol at 0.1, 1.0 and 10.0 μM (FIG. 5B). Hydroxytyrosol also showed significant increase in the activity of mitochondrial complex III, IV and V in adipocytes cells at 0.1 μM and 10 μM (FIGS. 5C, 5D and 5E).

Effect of Hydroxytyrosol on Cpt1 Gene Expression

CPT-1 is the gatekeeper of mitochondrial fatty acid oxidation because it regulates long-chain fatty acid transport across the mitochondrial membrane by converting acyl-CoA into acylcarnitine. HT showed dose-dependent increase on Cpt1 mRNA expressions significant increase at 1.0 μmol/l HT.

In summary hydroxytyrosol promotes mitochondrial activity and mitochondrial biogenesis leading to an enhancement of mitochondrial function and cellular defense system.

Example 2

Effect of Hydroxytyrosol on Endurance

The purpose of the study was to determine the effect of hydroxytyrosol on maximal running performance on a treadmill.

In short, forty mice (C57BL/6NCrl; 8 wks old) were purchased from Charles River (Sulzfeld, Germany) and housed individually with free access to water and feed, with an alternating 12-hour light-dark cycle. The animals were fed a standard rodent diet (Ssniff R/M-H, Ext. n° V1536, Ssniff Ltd., Soest, Germany) After 2 weeks of adaptation to the diet the mice were randomized according to body weight into four experimental groups of 10 animals. The four groups were treated orally every morning for 3 weeks with either water (control group) or with an olive extract diluted to 0.2 ml with water and containing 50% hydroxytyrosol at doses of 50, 150, or 300 mg/kg body weight per day. There was no difference in feed consumption over the whole experiment. After 3 weeks of treatment the maximal running distance on a treadmill was measured. Statistical significance of the mean differences between dietary groups was tested by one-way analysis of variance (ANOVA). If significant differences were found, the Dunnett's test for multiple comparison was used to compare each group to the control group. P values less than 0.05 were considered significant. Hydroxytyrosol significantly increased the running distance to exhaustion in mice and so improved endurance in prolonged exercise.

Figure 7:
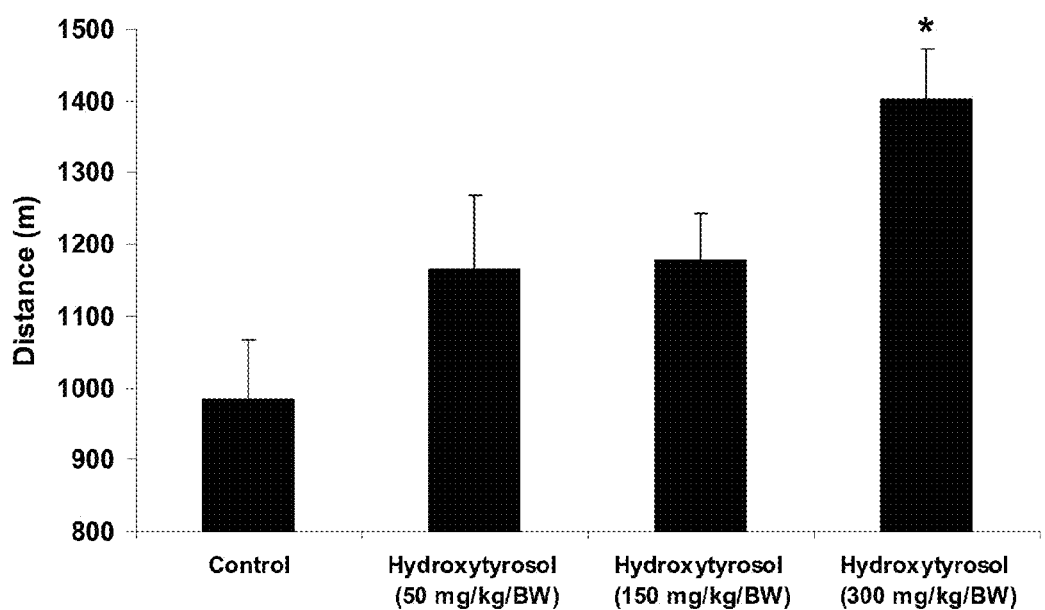
FIG. 7 Hydroxytyrosol, given as an olive extract containing 50% hydroxytyrosol at doses of 50, 150, or 300 mg/kg body weight per day by gavage, increases endurance by up to 50% in mice after 14 days of supplementation.

FIG. 7 shows the effect of Hydroxytyrosol, given as an olive extract containing 50% hydroxytyrosol at doses of 50, 150, or 300 mg/kg body weight per day by gavage, increases endurance by up to 50% in mice after 3 weeks of supplementation.

Example 3

An energy drink contains 50 mg hydroxytyrosol and 100 mg caffeine/serving.

Example 4

A sport supplement contains 20 g creatine and 100 mg hydroxytyrosol.

Example 5

A supplement for body shaping/fat burning/improving body composition contains 500 mg carnitine and 25 mg hydroxytyrosol/day and person Example 6

An energy shot, eg 5 hours, contains hydroytyrosol in addition to B vitamins, taurine, glucuronolactone, caffeine (or decaf, citicoline, malic acid, N-Acetyl tyrosine, L-Phenylalanine)

Example 7

A chocolate bar contains 25 mg hydroxytyrosol and 25 mg EGCG per 25 g chocolate.

Example 8

An instant sports beverage contains 5 g creatine, 50 mg CoQ10, and 50 mg hydroxytyrosol.

Example 9

An energy bar contains 5 mg resveratrol and 5 mg hydroxytyrosol.

Example 10

A ready to drink ice tea (thus containing EGCG) is fortified with 12.5 mg hydroxytyrosol and 5 mg resveratrol per 8 fl oz.

Example 11

Apple juice (thus containing quercetin) is fortified with 12.5 mg hydroxytyrosol and 5 mg resveratrol per 8 fl oz.

Example 12

A ready to drink sports beverage is fortified with 15 mg hydroxytyrosol, 2.5 mg resveratrol, 50 mg quercetin, and 25 mg EGCG per 8 fl oz.

Example 13

An energy shot is fortified with 25 mg hydroxytyrosol, 200 mg caffeine and 100% RDA of vitamins B1, B2, B3, B5, biotin, and B12 per 2 fl oz.

Example 14

A mini energy shot is designed as liquid praline/pocket coffee and is fortified with 25 mg hydroxytyrosol, 200 mg caffeine and 100% RDA of vitamins B1, B2, B3, B5, biotin, and B12 per 2 fl oz.

Example 15

Synergistic Effects of Hydroxytyrosol in Combination with Other Compounds

The objective of the experiment was to investigate whether and how mitochondrial energy production in myoblasts is affected by hydroxytyrosol alone or in combination with other compounds. For energy production, the mitochondrial electron transport chain generates a proton gradient across the mitochondrial intermembrane space, creating a membrane potential that powers the synthesis of ATP by the ATP synthase complex. Hence, the mitochondrial membrane potential is indicative of active mitochondrial energy production. The cationic green fluorescent compound JC-1

(5,5',6,6'-tetracholoro-1,1',3,3'-tetraethylbenzimidazolyl-carbocyanine iodide) is taken up by mitochondria proportionally to the inner mitochondrial membrane potential. If a critical concentration is reached, JC-1 forms aggregates, which changes its fluorescence properties from green to red fluorescence. Hence the ratio of red (aggregated) to green fluorescence (monomeric) is directly proportional to the mitochondrial membrane potential in stained cells, and serves as an indicator for the general health and function of the mitochondria. An increased mitochondrial membrane potential indicates an improved energetic state and increased capability to generate ATP and provide energy for other cellular components.

We examined the effect of hydroxytyrosol, caffeine, L-carnitine, or the combination of hydroxytyrosol with caffeine or L-Carnitine on the mitochondrial membrane potential in C2C12 mouse myoblasts. C2C12 cells were seeded into a 96-well cell culture plate at 1000 cells/well and cultured in growth medium (Dulbecco's modified eagle medium (DMEM) supplemented with 10% fetal bovine serum) in a standard incubator (humidified, 37° C., 5% $CO_2$) for 24 h. Cells were then incubated with growth medium containing a) control solvent (phosphate buffered saline), b) 1 uM hydroxytyrosol, c) 200 uM caffeine, d) 200 uM L-carnitine, e) 1 uM hydroxytyrosol+200 uM caffeine, or f) 1 uM hydroxytyrosol+200 uM L-carnitine. The AMP kinase activator aminoimidazole carboxamide ribonucleotide (AICAR) is known to affect mitochondrial energy production and served as positive control (500 uM). After 24 h of treatment, cells were incubated with medium containing JC-1 (2 ug/ml) for 30 min at 37° C., then the staining solution was removed, DMEM without phenol red was added, and green fluorescence (ex 485 nm/em 538 nm) and red fluorescence (ex 544 nm/em 590 nm) was measured using a fluorescence plate reader (SpectraMax M5). The ratio of red to green fluorescence in each well was determined and the average and standard deviation of the quadruplicate treatments were calculated.

Treatment of C2C12 cells with AICAR affected cellular energy production, causing an increase in mitochondrial potential which is reflected by an increase in red/green fluorescence ratio (FIG. 8A). Treatment of the cells with 1 uM hydroxytyrosol (HT) had no significant effect, while treatment with 10 uM HT increased mitochondrial potential (FIG. 8A). Treatment with 200 uM caffeine or 200 uM L-carnitine alone had no significant effect on mitochondrial membrane potential (FIG. 8B). However, when the compounds were employed at equivalent concentrations but in combination with 1 uM HT, a synergistic effect on mitochondrial membrane potential was observed. Treatment of C2C12 cells with the combination of hydroxytyrosol and caffeine, or the combination of hydroxytyrosol and L-carnitine increased mitochondrial membrane potential by 15% and 14%, respectively. This effect was comparable to the effect observed with AICAR (+16%) (Table I, below).

TABLE I

Increase in mitochondrial potential as assessed by relative JC-1 fluorescence

| Treatment | Increase in mitochondrial membrane potential |
|---|---|
| Control | ref. |
| 500 µM AICAR | 16% |
| 1 µM Hydroxytyrosol | 1% |
| 10 µM Hydroxytyrosol | 11% |
| 200 µM Caffeine | −4% |
| 200 µM L-carnitine | 0% |
| 200 µM Caffeine + 1 µM Hydroxytyrosol | 15% |
| 200 µM L-carnitine + 1 µM Hydroxytyrosol | 14% |

These results demonstrate that the combination of hydroxytyrosol and caffeine, and the combination of hydroxytyrosol and L-carnitine synergistically enhances mitochondrial function and energy production.

What is claimed is:

1. A method of increasing mitochondria biogenesis in a mammal comprising:
   (a) administering to the mammal in need of increased mitochondria biogenesis an effective amount of a composition comprising a dosage amount of 10-200 mg of hydroxytyrosol in combination with a dosage amount of 50-450 mg of caffeine; and
   (b) observing a mitochondria biogenesis effect.

2. The method according to claim 1, wherein the hydroxytyrosol is from an olive extract.

3. The method according to claim 1, wherein the composition is a nutraceutical or food composition.

4. The method according to claim 1, wherein the composition is a veterinary composition.

5. The method according to claim 1, wherein the mitochondria biogenesis effect comprises observations that the method helps reduce muscle fatigue; helps reduce muscle soreness; complements an immediate short term effect of caffeine with a sustained effect on energy generation; helps promote energy generation from fat; helps lower plasma lactate during exercise; helps maintain muscle force in conditions of oxidative stress; helps protect against exercise-induced oxidative stress; helps the body to find more energy without getting too much caffeine; gives long-lasting energy; helps boost body's own energy production; helps maintain more even energy levels throughout the day; provide for immediate and sustained energy; helps the body to adapt to exercise; helps prepare the body for exercise goals; helps revamp the body's shape; facilitates a restart of an exercise program; helps one to get going again; helps one feel more energetic; helps one feel more active; supports one's zest for action; helps one cope with a busy lifestyle; increased muscle work capacity; improved aerobic capacity; enhanced physical performance; enhanced exercise performance; improved running endurance; improved running distance and/or improved running time; or stimulates energy formation from nutrients.

6. The method according to claim 5, wherein the composition is a veterinary composition.

* * * * *